Figure 1:
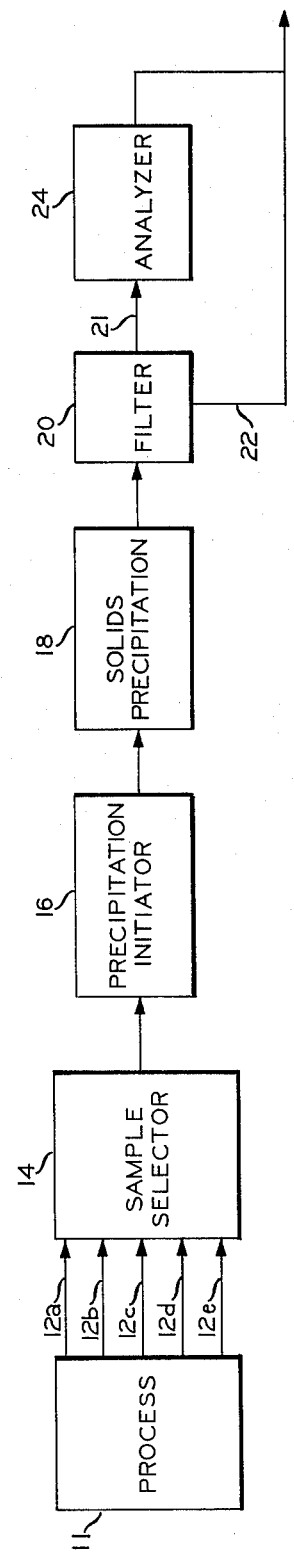

United States Patent [19]

Ririe, Jr.

[11] 4,229,971
[45] Oct. 28, 1980

[54] LIQUID SAMPLING SYSTEM
[75] Inventor: Otis E. Ririe, Jr., Bartlesville, Okla.
[73] Assignee: Phillips Petroleum Company, Bartlesville, Okla.
[21] Appl. No.: 572,043
[22] Filed: Apr. 28, 1975
[51] Int. Cl.³ ..................... G01N 31/08; G01N 33/22
[52] U.S. Cl. .................................. 73/61 R; 23/230 R
[58] Field of Search ............. 73/61.1 R, 61.1 C, 61 R, 73/53; 23/230 R, 253 R; 210/24 C, 198 C

[56] References Cited
U.S. PATENT DOCUMENTS

| | | | |
|---|---|---|---|
| 3,254,965 | 6/1966 | Ogle | 23/253 R X |
| 3,512,940 | 5/1970 | Shapiro | 73/61 R X |
| 3,558,277 | 1/1971 | Laman et al. | 23/230 R |
| 3,607,073 | 9/1971 | Stamm | 23/230 R |
| 3,860,393 | 1/1975 | Campen, Jr. | 23/230 R |
| 3,879,127 | 4/1975 | Storr et al. | 210/24 C X |

*Primary Examiner*—Daniel M. Yasich
*Assistant Examiner*—Joseph W. Roskos

[57] ABSTRACT

In preparing a sample of a liquid material, particularly a sample suitable for chromatographic analysis, an apparatus and method are provided whereby dissolved precipitatable material is removed from the liquid material by precipitation followed by filtering to obtain a liquid sample which can be suitably analyzed. In a preferred embodiment a combination of dilution and cooling are used to precipitate trinitrotoluene from a solution containing sulfuric and nitric acids prior to the chromatographic analysis of the remaining sample liquid material.

33 Claims, 2 Drawing Figures

LIQUID SAMPLING SYSTEM

This invention relates to an apparatus and method for sampling a liquid material. In another aspect the invention relates to an apparatus and method for preparation of a sample for chromatographic anaylsis. In yet another aspect the invention relates to an apparatus and method for sequentially sampling a plurality of liquid sample sources. In still another aspect the invention relates to an apparatus and method for preparing a liquid sample containing dissolved precipitatable material for chromatographic analysis. In another aspect the invention relates to an apparatus and method for preparing a sample for chromatographic analysis from a liquid material comprising dissolved explosive material.

The use of chromatographic analysis techniques for monitoring and controlling chemical processes or reactions is advantageous in conjunction with the optimization of process efficiency. Such analysis systems are particularly useful in conjunction with automatic or computerized control systems which can rapidly and efficiently analyze the information provided by a chromatographic analysis and initiate necessary process changes to maintain desired operating conditions. It is often desirable to analyze a liquid stream which contains liquid materials which are preferably excluded from the material which is to be introduced into analysis equipment such as a chromatographic analyzer. Such materials include those which would deleteriously interfere with the analysis process, those which by their inherent nature or by their presence within the analysis apparatus would present a safety hazard, or other materials which, for similar reasons, would be desirably excluded from the analysis apparatus. Such a problem exists, for example, in the analysis of liquid materials containing dissolved explosive materials such as trinitrotoluene, dinitrotoluene, and mononitrotoluene in the production of trinitrotoluene.

Accordingly, an object of the invention is to provide an apparatus and method for sampling a liquid material. Another object of the invention is to provide an apparatus and method for preparation of a sample for chromatographic analysis. Yet another object of the invention is to provide an apparatus and method for sequentially sampling a plurality of liquid sample sources. Still another object of the invention is to provide an apparatus and method for preparing a liquid sample containing dissolved precipitatable material for chromatographic analysis. Yet another object of the invention is to provide an apparatus and method for preparing a sample for chromatographic analysis from a liquid material comprising dissolved explosive material.

In accordance with the invention, a liquid sample for analysis of a liquid material containing dissolved constituents which are desirably not introduced into an analysis apparatus is prepared by precipitating the objectionable dissolved material, filtering the thus precipitated material from at least a portion of a sample, and utilizing the filtered liquid thereby obtained as a sample which can be analyzed to yield information relating to the original liquid material from which it was obtained. In accordance with the invention one of a plurality of liquid materials can be selected and a sample prepared therefrom. In a preferred embodiment of the invention, a sample for chromatographic analysis is prepared from a process liquid containing dissolved precipitatable material by cooling and diluting the liquid to precipitate the dissolved material, then filtering to remove the resulting solid precipitate from at least a portion of the diluted sample to produce an analysis sample which, although diluted, contains the same relative proportions of nonprecipitated liquid materials as did the original process liquid. Analysis of the filtered samples can therefore be accomplished to determine the ratios of certain constituents within the process liquid which in turn will yield information relating to the extent to which the reaction is complete and, particularly when compared on a time basis with similar analyses of other process streams, the rate at which the process is proceeding. In a preferred embodiment the invention provides means by which the apparatus of the invention can be flushed and purged to insure both safe operation of the apparatus and the capability for safe maintenance, repair, or replacement of various apparatus components.

Figure 2:
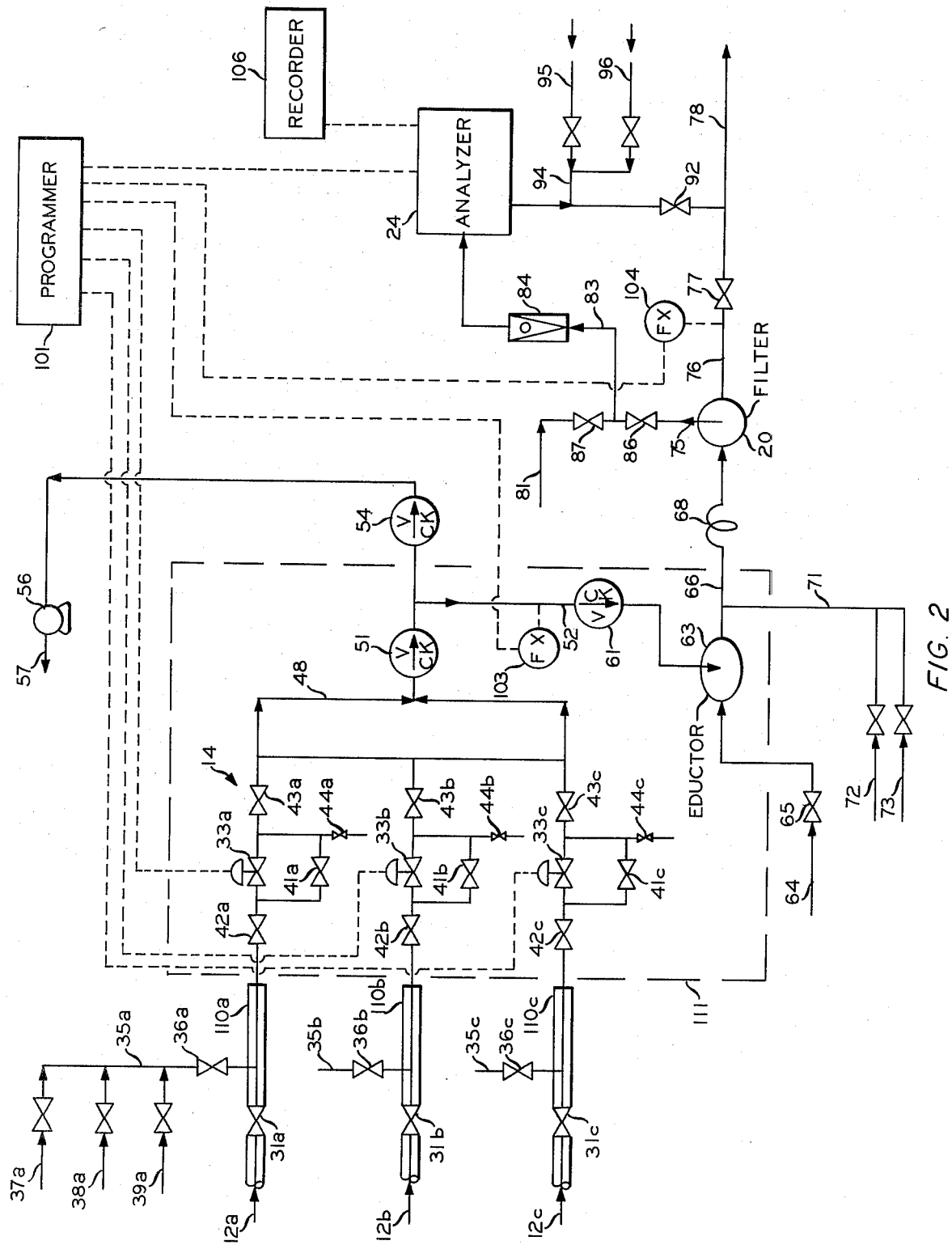

Other objects and advantages of the invention will be apparent from the specification and claims including a description of the drawings in which:

FIG. 1 is a block diagram of a preferred method and apparatus of the invention; and FIG. 2 is a schematic illustration of a presently preferred embodiment of the apparatus and method of FIG. 1.

Referring to FIG. 1 there is illustrated a process 11 having a plurality of liquid material streams or other liquid material sources which it is desired to analyze. A plurality of process liquid conduits 12a, 12b, 12c, 12d, 12e communicate with these liquid sources within the process 11 and provide fluid communication between the process and a sample selector 14. The sample selector 14 provides fluid communication between a selected one of the process liquid conduits 12a–12e and a precipitation initiator means 16. The precipitation initiator means 16 acts upon the sample from the conduit 12a–12e selected by the sample selector 14 to establish conditions under which precipitatable material dissolved within the sample from the selected process liquid conduit 12a–12e will precipitate to form a solid precipitate. Precipitation continues in a solids precipitation means 18 wherein conditions are maintained to favor the continuing precipitation of solid materials from the sample. The remaining liquid containing the solid precipitate is passed to a filter means 20. The filter 20 separates the material received from the solids precipitation means 18 into an analysis sample stream 21 substantially free of precipitated solid material and a solids removal stream 23. The analysis sample stream 21 is conveyed to a suitable analyzer means 24 for analysis. The spent analysis sample from the analyzer means 24 as well as the solids removal stream 22 are then disposed of in an acceptable manner or, where appropriate, recycled to the process 11.

FIG. 2 illustrates an apparatus and method which are presently preferred in the practice of the invention when the precipitatable material to be removed from the process liquid can be precipitated by cooling and by diluting the process liquid. A plurality of process liquid conduit means 12a, 12b, 12c are in communication with appropriate liquid material sources within a process to provide a flow of process liquid material through respective shutoff valves 31a, 31b, 31c to a sample selector means 14 comprising respective automatically actuated selecting valves 33a, 33b, 33c.

In order to permit flushing and purging of the sample selector 14 and other sample handling equipment, a respective purge conduit means 35a, 35b, 35i c communicates with each process liquid conduit means 12a, 12b, 12c downstream of its shutoff valve 31a, 31b, 31c through a respective purge valve 36a, 36b, 36c. Each purge conduit means 35a, 35b, 35c is in turn provided with means to permit fluid communication with wash fluid supply conduits such as a nitrogen supply conduit 37a, a water supply conduit 38a, and an acid supply conduit 39a. A bypass valve 41a, 41b, 41c is connected in parallel fluid communication with each respective selector valve 33a, 33b, 33c. Immediately upstream of each selector valve-bypass valve parallel combination is a respective blocking valve 42a, 42b, 42c, and immediately downstream from each such parallel valve pair is a respective blocking valve 43a, 43b, 43c. In addition, a drain valve 44a, 44b, 44c can be associated with each respective selector valve-bypass valve combination as illustrated.

In normal operation of the apparatus to select and prepare a suitable analysis sample from process liquids, shutoff valves 31a, 31b, 31c will be in an open position, purge valves 36a, 36b, 36c will be closed, blocking valves 42a, 42b, 42c will be open, blocking valves 43a, 43b, 43c will be open, bypass valves 41a, 41b, 41c will be closed, and drain valves 44a, 44b, 44c will be closed. In selecting a process liquid stream to be sampled, one of the selector valves 33a, 33b, 33c will be maintained in an open position and all remaining selector valves will be maintained in a closed position. In normal operation of the apparatus, therefore, each selector valve 33a, 33b, 33c will control fluid communication between its respective process liquid conduit 12a, 12b, 12c and a parallel flow loop conduit means 48.

Process liquid material entering the parallel flow loop 48 through an open selector valve will divide and flow both directions around the loop and exit the parallel flow loop 48 through a check valve 51. The parallel flow of the process liquid through the parallel flow loop 48 effectively precludes the retention within the apparatus of process liquid material from a previously selected process liquid conduit 12a, 12b, 12c. The liquid material flowing through the check valve 51 is delivered to a process sample conduit 52. If necessary or desirable to insure maintenance of a fresh process liquid sample within the process sample conduit 52, flow through the selected process liquid conduit 12a, 12b, 12c and the parallel flow loop 48 can be increased by withdrawing a desired amount of liquid material through a check valve 54 and recycling the thus withdrawn liquid to the process using a suitable pump means 56 and recycle conduit 57.

The process sample liquid within the process sample conduit 52 flows through a check valve 61 to an eductor 63 where it is cooled and diluted by a flow of suitable liquid, such as water, from an eductor diluent inlet conduit 64. A valve 65 in the eductor diluent inlet conduit 64 permits adjustment of the rate of flow of diluent through the eductor. The eductor outlet conduit 66 provides fluid communication for the diluted process sample between the eductor 63 and a precipitation conduit 68. The precipitation conduit 68 can be any suitable conduit of adequate size and volume to permit effective precipitation of dissolved material within the process sample liquid during passage of the diluted process sample liquid therethrough. While a suitable length of conduit is preferred for this purpose, a vessel of adequate size to permit effective precipitation but small enough to avoid unnecessary delay in producing an analysis sample can be used.

A purge conduit means 71 communicating with the eductor outlet conduit 66 permits introduction of wash fluids to clean and flush the precipitation conduit 68 and filter 20 as necessary to prevent accumulation of precipitated material therein. A plurality of wash fluid supply conduits such as a water supply conduit 72 and an acid supply conduit 73 can be used to provide a wash fluid to the purge conduit 71 when flushing of the precipitation conduit 68 and filter 20 is desired.

A filtered liquid conduit 75 delivers an essentially precipitate-free analysis sample liquid from the filter 20. A filter bypass conduit 76 carries the remaining liquid material and the solid precipitate from the filter 20 through a valve 77 to a disposal conduit 78.

A calibration sample conduit 81 is connected to an appropriate source of a standard sample liquid which can be utilized to check the calibration of the analyzer 24 as required. An analyzer inlet conduit 83 having a flow measuring device such as a rotometer 84 located therein communicates with the filtered liquid effluent conduit 75 through valve 86 and with the calibration sample conduit 81 through a valve 87. During calibration of the analyzer 24, the valve 86 is closed and the valve 87 is opened. During analysis of a sample from the filter 20, the valve 87 is closed and the valve 86 is open. Material entering the analyzer through the analyzer inlet 83 is analyzed to determine the ratios of preselected constituents within the sample. Liquid which has been analyzed and excess liquid which is not required for analysis is directed to an analyzer outlet conduit 91 and through a valve 92 to the disposal conduit 78. A purge conduit means 94 communicates with the analyzer outlet conduit 91 for providing wash fluids such as water from a water supply conduit 95 and acid from an acid supply conduit 96 to clean and flush the analyzer outlet conduit 91 and the disposal conduit 78.

A programmer means 101 is utilized to control the automatic operation of the sampling apparatus by controlling the opening and closing of the selector valves 33a, 33b, 33c, and by monitoring the flow of liquid through the system as observed by a flow sensor 103 associated with the process sample conduit 52 and a flow sensor 104 associated with the filter bypass conduit 76. The signal delivered to the programmer 101 by the flow sensor 103 can be utilized to monitor operation of the sample selector means 14 since the presence of flow within the process sample conduit 52 while all selector valves 33a, 33b, 33c are closed will indicate a leak in a selector valve 33a, 33b, 33c or bypass valve 41a, 41b, 41c, and the absence of flow through the process sample conduit 52 when a selector valve 33a, 33b, 33c has been opened by the programmer 101 will indicate a blockage somewhere in the selected stream. In a similar manner the signal delivered to the programmer 101 by the flow sensor 104 can be used to initiate an alarm or suitable corrective action if the filter 20 should become plugged. The use of other suitable flow sensing devices at appropriate locations within the sample preparation system of the invention is also within the scope of the invention.

The results of the analysis performed by the analyzer 24 can be communicated to a recorder means 106 or can be communicated to the programmer 101 through the lines of communication between the analyzer 24 and programmer 101, or can be provided to both a recording device 106 and the programmer 101 as well as to additional control apparatus, visual display apparatus, and the like.

When the diluent introduced into the eductor 63 to dilute the process sample is also utilized to cool the process sample, maintenance of the process liquid prior to the dilution and cooling thereof at a desired temperature is preferably attained by utilizing heated jacket means 110a, 110b, 110c on the process liquid conduits and enclosing other equipment handling the undiluted process liquid within a heated enclosure 111. In addition, the same means used to heat the process liquid conduit 12a, 12b, 12c such as for example steam traced conduits, can be utilized to maintain the check valve 54, pump means 56, and return conduit 57 at a desired temperature.

In operation, the programmer 101 actuates a preselected selector valve 33a, 33b, 33c to provide fluid communication between the associated process liquid conduit 12a, 12b, 12c and the parallel flow loop 48 while maintaining all other selector valves in a closed position. Flow from the selected process liquid conduit 12a, 12b, 12c is therefore established through the process sample conduit 52 to the eductor 63 where a suitable diluent liquid is utilized to dilute and cool the process sample from the process sample conduit 52 to initiate precipitation of precipitatable materials dissolved in the process liquid sample. Precipitation of the desired material is carried out in the precipitation conduit 68 after which the filter 20 removes the precipitated material from a portion of the liquid flowing therethrough. The precipitate-free liquid effluent from the filter is passed via the filter liquid effluent conduit 75 and analyzer inlet conduit 83 to the analyzer 24. After a sufficient time has elapsed to insure the presence of a representative sample within the analyzer 24, analysis of the sample is initiated by the analyzer 24 in response to a signal from the programmer 101. The programmer 101 then closes the previously open selector valve and opens another selector valve 33a, 33b, 33c to initiate subsequent analysis of an additional process liquid stream. Operation in this manner is continued to sequentially analyze the contents of each process stream. Although the invention has been illustrated in conjunction with a system employing three process liquid conduits 12a, 12b, 12c, the use of any number of such process liquid conduits is within the scope of the invention.

The apparatus and method of the invention are particularly useful in the analysis of liquids containing dissolved high explosive material. For example, in the production of trinitrotoluene, nitration of toluene is carried out in the presence of sulfuric and nitric acids, and it is desirable to be able to determine the ratio of sulfuric acid to nitric acid within selected process streams in order to determine the degree of completion of the nitration reaction and the rate at which the process is progressing. In the analysis of such process liquids, it is necessary to avoid the presence of undissolved nitrated and partially nitrated toluenes in any portion of the apparatus associated with the system since such a presence carries with it the hazard of an explosion. All process liquid conduits 12a, 12b, 12c carrying process liquids are therefore steam traced and the heated enclosure 111 within which all undiluted process liquids are handled is steam heated in order to maintain the process liquids at a temperature sufficient to insure maintenance of the dissolved explosives in solution. In view of the corrosive and explosive nature of the process liquids, all equipment is suitably lined with polytetrafluoroethylene or another similar material such as Kel-F, Viton, or No. 316L stainless steel to protect against corrosion. In order to safeguard against electrically triggered explosions, no metal to metal contact is made at any point in contact with the sample or where accidental deposits of explosive could accumulate due to leaks or spills. As previously described any line within the sample selector 14 can be flushed with fresh acid followed by water and then purged with nitrogen before disconnecting any line or component for maintenance. Flow through the apparatus is preferably provided by a gravity head although a pump means (not illustrated) can be utilized where necessary. The diluent utilized to operate the eductor 63 is preferably water. The water cools and dilutes the sample to precipitate the dissolved nitrated and partially nitrated toluenes. The water also provides additional stream pressure to assist in obtaining flow through the filter 20. The precipitated explosive crystals are separated by the filter 20 to provide a substantially explosive-free liquid effluent as an analysis sample to the analyzer 24. Although the liquid of the analysis sample has been diluted by the water introduced by the eductor 63, the ratio of nitric acid to sulfuric acid within the analysis sample delivered to the analyzer 24 is the same as the ratio of nitric acid to sulfuric acid in the undiluted process liquid.

Specific equipment which can be utilized in the construction of a system as illustrated by FIG. 2 for analyzing corrosive and explosive constituents are as follows:

| Appartus | Manufacturer |
|---|---|
| All non-automatic valves | Nupro Type T-4VD2 Nupro Co. 15635 Saranac Pl. Cleveland, Ohio 44110 |
| Selector valves 33a,33b,33c | Mace Model No. 909-0001 Mace Co. 2413 Lee Ave. South El Monto, Calif. 91733 |
| Check valves 51,54,61 | Model No. FCV144, ⅛ NPT Flurocarbon Company, 1432 S. Allec St. Anaheim, Calif. 92803 |
| Eductor 63 | Air Vac Model LQT-110 Teflon Gems Safe Pak Air Vac Engineering Co., Inc. 100 Gulf St. Milford, Conn. 06460 |
| Filter 20 | Swirlclean Filter, all Teflon with Viton O rings Collins Products Co. P. O. Box 382 Livingston, Tex. 77351 |
| Flow sensors, 103, 104 | Valcor Model No. 400T2HF Valcor Engineering Corp. 3655 Carnegie Ave. Kenilworth, N.J. 07033 |
| Rotometer 84 | Brooks-Mite Model 2102 with Tube No. 4-385 Emerson Electric Co. Brooks Instrument Div. 407 W. Vine St. Hatfield, Pa. 19440 |
| Analyzer 24 | Optichrom/LC Liquid Chromatographic Analyzer Applied Automation Inc. Bartlesville, Oklahoma |
| Programmer 101 | Chromatographic Analysis Programmer Model 102 Applied Automation, Inc. Bartlesville, Oklahoma |

When a chromatographic programmer 101 such as the Model 102 programer listed above is utilized to initiate pneumatic signals as required for the preferred selector valve 33a, 33b, 33c, it will be desirable to employ, in addition to the programmer which produces an electrical signal, a suitable source of pneumatic pressure from which the actuating signal to the selector valve can be produced. With the above-listed analyzer 24 and programmer 101, the programmer 101 will ordinarily communicate with the selector valve 33a, 33b, 33c via the analyzer 24 in order to convert the programmer's electrical signal into a pneumatic signal suitable for operating the preferred selector valves.

Although the apparatus and method of the invention have been described in conjunction with a preferred embodiment wherein the process liquid is both cooled and diluted in order to precipitate dissolved materials which are to be excluded from the analyzer 24, other means for initiating precipitation of dissolved constituents such as cooling without dilution, dilution without cooling, addition of a precipitating agent, and the like can be readily adapted by those skilled in the art to be utilized in conjunction with the disclosed apparatus and method and are considered to be within the scope of the invention. Likewise, the use of the apparatus and method of the invention to prepare analysis samples and to analyze a wide variety of liquid materials can be practiced by those skilled in the art and is considered to be within the scope of the invention. Other reasonable variations and modifications are possible by those skilled in the art in accordance with the preceding description of the invention and the appended claims thereto without departing from the scope of the invention.

I claim:

1. Apparatus comprising:
   at least one sample conduit means for providing a liquid sample material containing precipitatable material in solution;
   means for initiating precipitation of said precipitatable material from said liquid sample material;
   filter means for separating from the precipitated material at least a portion of the remaining liquid of said liquid sample material;
   and liquid chromatographic analysis means for analyzing said portion of said remaining liquid material;
   wherein said means for initiating precipitation comprises means for cooling said liquid sample material.

2. Apparatus in accordance with claim 1 wherein said means for initiating precipitation comprises means for simultaneously cooling and diluting said liquid sample material.

3. Apparatus in accordance with claim 1 wherein there are a plurality of said sample conduit means, said apparatus additionally comprising sample selector means for delivering liquid sample material from a preselected one of said sample conduit means to said means for initiating precipitation.

4. Apparatus in accordance with claim 3 wherein said means for initiating precipitation comprises means for simultaneously cooling and diluting said liquid sample material.

5. Apparatus comprising:
   at least one sample conduit means for providing a liquid sample material containing precipitatable material in solution;
   means for initiating precipitation of said precipitatable material from said liquid sample material;
   filter means for separating from the precipitated material at least a portion of the remaining liquid of said liquid sample material;
   and liquid chromatographic analysis means for analyzing said portion of said remaining liquid material; wherein said means for initiating precipitation comprises means for diluting said liquid sample material.

6. Apparatus in accordance with claim 5 wherein there are a plurality of said sample conduit means, said apparatus additionally comprising sample selector means for delivering liquid sample material from a preselected one of said sample conduit means to said means for initiating precipitation.

7. Apparatus comprising:
   a plurality of first conduit means for providing a plurality of liquid material streams each containing precipitatable material in solution;
   sample selector means associated with each said first conduit means for selecting and delivering one of said liquid material streams as a sample stream to a second conduit means; precipitation initiating means for cooling and diluting said sample stream received from said sample selector means via said second conduit means and delivering a diluted sample stream to a third conduit means;
   filter means communicating with said third conduit means for accepting said diluted sample stream and dividing said diluted sample stream into a sample liquid stream consisting essentially of diluted, unprecipitated sample material and a sample bypass stream comprising precipitated sample material; and
   fourth conduit means communicating with said filter means for removing said sample liquid stream from said filter means.

8. Apparatus in accordance with claim 7 additionally comprising chromatographic analysis means in fluid communication with said fourth conduit means for analyzing said sample liquid stream.

9. Apparatus in accordance with claim 7 wherein each said first conduit means comprises a heated sample conduit, said apparatus additionally comprising means for heating said sample selector means and said second conduit means.

10. Apparatus in accordance with claim 7 wherein said precipitation initiating means comprises an eductor.

11. Apparatus in accordance with claim 7 wherein said sample means comprises an automatically actuated first valve means associated with each said first conduit means wherein said second conduit means comprises a parallel flow loop conduit means in fluid communication with each said first valve means and an undiluted sample conduit in fluid communication between said loop conduit means and said precipitation initiating means.

12. Apparatus in accordance with claim 11 additionally comprising a programming means for initiating the opening of one of said first valve means at a time in a preselected timed sequence.

13. Apparatus in accordance with claim 12 additionally comprising a flow detection means associated with said undiluted sample conduit for delivering to said programming means a signal indicative of the presence or absence of flow through said undiluted sample means.

14. Apparatus in accordance with claim 13 additionally comprising check valve means associated with said undiluted sample conduit to prevent flow through said undiluted sample conduit toward said loop conduit means.

15. Apparatus in accordance with claim 14 additionally comprising first purge conduit means associated with each said first conduit means for introducing wash fluids into each said first conduit means and second purge conduit means associated with said third conduit means for introducing wash fluids into said third conduit means.

16. Apparatus in accordance with claim 15 additionally comprising a bypass valve connected in parallel with each said first valve means, a first blocking valve immediately upstream of the first valve-bypass valve parallel combination, a second blocking valve immediately downstream of said first valve-bypass valve parallel combination, and a drain valve means for draining material from said first valve-bypass valve parallel combination.

17. Apparatus in accordance with claim 16 wherein said precipitation initiating means comprises an eductor.

18. Apparatus in accordance with claim 17 wherein each said first conduit means comprises a heated sample conduit, said apparatus additionally comprising means for heating said sample selector means and said second conduit means.

19. Apparatus in accordance with claim 18 additionally comprising chromatographic analysis means in fluid communication with said fourth conduit means for analyzing said sample liquid stream.

20. A method for automatically determining the relative proportions of at least two liquid constituents in at least one liquid source comprising said at least two liquid constituents and dissolved precipitatable material, said method comprising:
removing a material sample from a selected one of said at least one liquid source;
precipitating said dissolved precipitatable material within said material sample from solution;
removing the precipitated material from at least a portion of said material sample to produce a liquid analysis sample; and
analyzing said analysis sample to determine the relative proportions of said at least two liquid constituents therein.

21. A method in accordance with claim 20 wherein said step of removing a liquid sample comprises establishing fluid communication with a preselected one of a plurality of liquid sources and removing a material sample from the thus selected liquid source.

22. A method in accordance with claim 21 additionally comprising sampling another of said liquid sources in a preselected sequence following analysis of the analyzer sample derived from the previously selected liquid source.

23. A method in accordance with claim 20 wherein precipitating said dissolved precipitatable material comprises cooling said material sample.

24. A method in accordance with claim 20 wherein precipitating said dissolved precipitatable material comprises simultaneously cooling and diluting said material sample to produce a diluted sample and wherein removing said precipitated material to produce said analysis sample comprises removing said precipitated material from at least a portion of said diluted sample to produce said liquid analysis sample.

25. A method in accordance with claim 24 wherein simultaneously cooling and diluting said material sample comprises introducing said material sample into a dilution liquid stream by means of an eductor.

26. A method in accordance with claim 25 additionally comprising recording the relative proportions of said at least two liquid constituents.

27. A method in accordance with claim 25 wherein said dissolved precipitatable material comprises a dissolved explosive material and wherein said at least two liquid constituents comprise at least two acid liquids.

28. A method in accordance with claim 27 wherein said explosive material comprises trinitrotoluene, wherein said at least two acid liquids comprise sulfuric acid and nitric acid, and wherein said dilution liquid comprises water.

29. A method in accordance with claim 28 wherein said step of removing a liquid sample comprises establishing fluid communication with a preselected one of a plurality of liquid sources and removing a material sample from the thus selected liquid source.

30. A method in accordance with claim 29 additionally comprising sampling another of said liquid sources in a preselected sequence following analysis of the analyzer sample derived from the previously selected liquid source.

31. A method in accordance with claim 20 wherein said dissolved precipitatable material comprises a dissolved explosive material and wherein said at least two liquid constituents comprise at least two acid liquids.

32. A method in accordance with claim 31 wherein said explosive material comprises trinitrotoluene, wherein said at least two acid liquids comprise sulfuric acid and nitric acid.

33. A method in accordance with claim 20 wherein precipitating said dissolved precipitatable material comprises diluting said material sample.

* * * * *